US012721721B2

(12) United States Patent
Gerlach

(10) Patent No.: US 12,721,721 B2
(45) Date of Patent: Sep. 1, 2026

(54) DIFFRACTIVE EYE LENS

(71) Applicant: Carl Zeiss Meditec AG, Jena (DE)

(72) Inventor: Mario Gerlach, Glienicke-Nordbahn (DE)

(73) Assignee: Carl Zeiss Meditec AG, Jena (DE)

( * ) Notice: Subject to any disclaimer, the term of this patent is extended or adjusted under 35 U.S.C. 154(b) by 795 days.

(21) Appl. No.: 17/904,103

(22) PCT Filed: Feb. 8, 2021

(86) PCT No.: PCT/EP2021/052923
§ 371 (c)(1),
(2) Date: Jan. 13, 2023

(87) PCT Pub. No.: WO2021/160548
PCT Pub. Date: Aug. 19, 2021

(65) Prior Publication Data

US 2023/0190453 A1 Jun. 22, 2023

(30) Foreign Application Priority Data

Feb. 13, 2020 (DE) ......................... 102020201817.0

(51) Int. Cl.
*A61F 2/16* (2006.01)
*B29D 11/00* (2006.01)
*G02C 7/04* (2006.01)

(52) U.S. Cl.
CPC ...... *A61F 2/1656* (2013.01); *B29D 11/00038* (2013.01); *G02C 7/045* (2013.01);
(Continued)

(58) Field of Classification Search
CPC .............. A61F 2/1656; A61F 2240/001; A61F 2250/0053; B29D 11/00038; G02C 7/045;
(Continued)

(56) References Cited

U.S. PATENT DOCUMENTS

2010/0324165 A1 12/2010 Ritter et al.

FOREIGN PATENT DOCUMENTS

CN 110753528 2/2020
DE 102007059470 B3 5/2009
(Continued)

OTHER PUBLICATIONS

International Search Report (translation provided) and Written Opinion for International Application No. PCT/EP2021/052923 date mailed May 14, 2021.
(Continued)

*Primary Examiner* — Tuyen Tra
(74) *Attorney, Agent, or Firm* — DeWitt LLP

(57) ABSTRACT

A diffractive eye lens having a front side, a rear side and an optical main axis, wherein the front side and/or the rear side has a spherical, an aspherical, a spherical-toric or an aspherical-toric basic shape, and the front side and/or the rear side has a diffractive optical structure. The diffractive eye lens allows for color correction and simultaneously improves visual properties by reducing a halo. The diffractive optical structure in a first lens region is designed such that, at a design wavelength, there is a significant diffraction efficiency for a phase deviation between the first main sub-zones of more than one wavelength and, for the first lens region, On average over all diffraction zones, a proportion of the main sub-zones on the diffraction zones is for example at least 94%, at least 95% and at best nearly 100%.

20 Claims, 5 Drawing Sheets

(52) U.S. Cl.
CPC . *A61F 2240/001* (2013.01); *A61F 2250/0053* (2013.01); *G02C 2202/20* (2013.01)

(58) Field of Classification Search
CPC .... G02C 2202/20; G02C 7/042; G02C 7/044; G02B 5/1895; G02B 5/1876
See application file for complete search history.

(56) References Cited

FOREIGN PATENT DOCUMENTS

| | | | |
|---|---|---|---|
| EP | 2440962 | B1 | 4/2012 |
| WO | WO9744689 | | 11/1997 |
| WO | WO0104667 | | 1/2001 |
| WO | WO2010093975 | | 8/2010 |
| WO | WO 2010/144315 | A1 | 12/2010 |
| WO | WO2011092169 | | 8/2011 |
| WO | WO 2014/033543 | A2 | 3/2014 |
| WO | WO2014033543 | | 3/2014 |
| WO | WO201850236 | | 8/2018 |
| WO | WO 2019/020435 | | 1/2019 |

OTHER PUBLICATIONS

Xie, "Design, Fabrication and Testing of Diffractive Multifocal Intraocular Lens (MIOL)," The University of Arizona University Libraries, UA Campus Repository, dated Sep. 23, 2024, 261 pages.
Chinese Search Report for Chinese Application No. 202180014536.7, dated Jan. 31, 2026, 9 pages.

1.0
0.5
0.1
0.05
0.01
0.005
0.500
0.100
0.050
0.010
0.005
-50
-40
-30
-20
-10
0
10

1.0
0.5
0.1
0.05
0.01
0.005
0.500
0.100
0.050
0.010
0.005
-50
-40
-30
-20
-10
0
10

1.0
0.5
0.1
0.05
0.01
0.005
0.500
0.100
0.050
0.010
0.005
-50
-40
-30
-20
-10
0
10

DIFFRACTIVE EYE LENS

RELATED APPLICATIONS

This application is a National Phase entry of PCT Application No. PCT/EP2021/052923 filed Feb. 8, 2021, which application claims the benefit of priority to DE Application No. 10 2020 201 817.0 filed, Feb. 13, 2020, the entire disclosures of which are incorporated herein by reference.

TECHNICAL FIELD

The present invention relates to a diffractive eye lens having a front side, a back side and a principal optical axis, with the front side and/or the back side having a spherical, an aspherical, a spherical-toroidal, an aspherical-toroidal or a free-form-shaped basic form, and the front side and/or the back side having a diffractive optical structure, the diffractive optical structure comprising a first lens region with a plurality of first ring-shaped diffraction zones circumferential the principal optical axis of the eye lens, each diffraction zone having a principal sub-zone and a phase sub-zone.

BACKGROUND

The use of diffractive structures for producing an optical power in eye lenses has been established for many years now and has been implemented in commercial products. This applies in particular to multifocal eye lenses or to eye lenses providing an extended depth of focus—so-called EDOF lenses. Bifocal eye lenses generally have two principal refractive powers and facilitate sharp vision in the distance (distance focus for looking into the distance) and at the reading distance (near focus for near vision). Multifocal eye lenses having more than two principal refractive powers for example facilitate additionally sharp vision at a mid-distance (intermediate vision). Bifocal or trifocal eye lenses are realized for example by diffractive structures that operate in a combination of different orders of diffraction.

Multifocal lenses having refractive and diffractive optical powers are known from EP 1 194 797 B1. The lenses disclosed there have annular or ring-shaped zones, with said annular zones being subdivided into in each case a principal sub-zone and a phase sub-zone. The system of the principal sub-zones constitutes a diffraction lens, which in this prior art has two principal refractive powers or main refractive powers. The refractive powers in the phase sub-zones are chosen such that the averaged refractive power of the entire zone or of the entire lens corresponds to one of the two principal diffractive powers. The described diffractive lens is a bifocal lens. EP 1 194 797 B1 furthermore describes trifocal lenses in which the averaged refractive power is equal to the central one of the three principal powers (mid distance), with the largest principal power being given by the +1st order diffractive power (reading distance, near vision) and the smallest principal power being given by the −1st order diffraction power (distance, distance focus). Such trifocal lenses can have a longitudinal chromatic aberration—also referred to as longitudinal color aberration—both in the smallest and in the largest of the three principal powers or main powers. If such lenses are intended to be used as ophthalmic lenses (e.g., contact lenses, intraocular lenses), then this longitudinal chromatic aberration is disadvantageous particularly for the smallest of the principal powers. This refractive power is used to image far-away objects. A longitudinal chromatic aberration accompanying the −1st order of diffraction is especially bothersome for such use as it further amplifies the natural longitudinal chromatic aberration of the eye.

To avoid an amplification of longitudinal chromatic aberrations, use is made of multifocal lenses that operate in combination of the zeroth, first and optionally second order of diffraction. The zeroth order of diffraction is used for the far focus in these lenses whereas the positive orders of diffraction (n>0) produce the addition powers for near vision and/or intermediate vision. The zeroth diffractive order of diffraction has the property of introducing no diffractive chromatic aberrations into the optical system of the eye. This means that distance vision is impaired by the purely refractive chromatic aberrations from the material dispersion of the optical media in the eye and the (artificial) eye lens. These chromatic aberrations can reduce the perceivable contrast of the patient in the case of polychromatic illumination. To reduce this loss of contrast there has been the development of multifocal diffraction lenses that facilitate a correction of the longitudinal chromatic aberrations even in the distance focus. By way of example, WO 2014/033543 discloses diffraction lenses that operate in higher orders of diffraction (n>0)—for example, in the +1st order of diffraction for the distance, in the +2nd order of diffraction for the intermediate range, and in the +3rd order of diffraction for near vision.

These are what are known as multi-order phase plates or MOD (multi order diffraction) optical units. The use of higher orders of diffraction is facilitated by a phase shift (also referred to as path length difference or optical path length difference below) of more than one wavelength (taking account of the respective refractive indices upstream and downstream of the boundary surface) between the annular diffraction zones of the MOD optical unit.

However, it was found that multifocal diffraction lenses embodied as an MOD optical unit with a phase shift of more than one wavelength produce significantly more “halo-like” stray light than multifocal lenses that realize the distance focus using the zeroth order of diffraction. In this case, a halo should be understood to mean halation which emerges in an overexposed background around a (punctiform) light source. In the radial direction, an unavoidable primary halo which arises from the superposition of the circles of confusion of the used orders of diffraction is adjoined by a secondary halo (also referred to as “deep halo” or “glow”). The latter leads to visual impairment of the user of the described diffraction lens and for example reduces contrast sensitivity.

SUMMARY OF THE INVENTION

Example embodiments of the present invention include a diffractive eye lens which facilitates a chromatic correction and simultaneously improves the visual properties of the eye lens by reducing a halo.

A first aspect of the invention relates to a diffractive eye lens having a front side, a back side and a principal optical axis. In this case, the front side and/or the back side have/has a spherical, an aspherical, a spherical-toroidal, an aspherical-toroidal or a free-form-shaped basic form. In this case, a free-form-shaped surface corresponds to a free form surface described for example by way of a polynomial or in piecewise fashion by way of polynomials. Further, the front side and/or the back side has/have a diffractive optical structure, the diffractive optical structure comprising a first lens region with a plurality of first ring-shaped diffraction zones circumferential the principal optical axis of the eye lens, each diffraction zone having a principal sub-zone and a phase sub-zone. The diffractive eye lens according to the invention is characterized in that the diffractive optical structure in the first lens region is designed such that at a design wavelength there is a significant diffraction efficiency for an optical path length difference between the first principal sub-zones of more than one wavelength. In the first lens region, the diffractive optical structure is furthermore designed such that averaged over all diffraction zones the principal sub-zones make up a proportion of the diffraction zones of at least 94%, in particular at least 95%, for the first lens region.

The front side and the back side of the diffractive eye lens according to the invention are responsible for the optical imaging properties. Light can penetrate into the eye lens on the front side and leave said eye lens again from the back side. The principal optical axis is perpendicular to an imaginary plane situated between the front side and the back side of the eye lens.

A diffractive optical structure should be understood to mean a boundary surface between two media with different refractive indices (for example lens material and aqueous humor) designed such that light is diffracted when passing through the boundary surface and interferes constructively. Typically, the surface has edges and consequently has a discontinuity in the gradient of the boundary surface at these edges (within the scope of the manufacturing tolerances and the employed tools).

If the optical power of a boundary surface with a diffractive optical structure for light guided into the zeroth order of diffraction is considered, the same optical power can also be produced by a boundary surface without a diffractive optical structure. Such a (imaginary) boundary surface without a diffractive optical structure is referred to as the basic form. The basic form can correspond to an imaginary connection of local maxima (in a height profile) of the diffractive optical structure.

If the basic form has a boundary surface without a diffractive optical structure, the basic form is the form of the surface itself.

The basic forms of the front side and the back side consequently determine the refractive power that the diffractive eye lens exhibits for light that is directed into the zeroth order of diffraction of the diffractive optical structure.

Since a side (front side, back side) of the eye lens having a diffractive optical structure may have one of the aforementioned basic forms, the diffractive optical structure is overlaid on the latter. Light directed into orders of diffraction that differ from zero ($n \neq 0$) is subject—as described below—to a refractive power that deviates from the refractive power of the basic form. This refractive power (caused by the diffractive optical structure) is typically referred to as additive power—also “add power”.

The diffractive optical structure has a first lens region which comprises a plurality of first diffraction zones which are arranged in ring-shaped fashion circumferential the principal optical axis of the eye lens. In this context, a lens region should be understood to mean a circular or circular-ring-shaped (annular) region of the lens. A lens region may also have a plurality of non-contiguous circular or circular-ring-shaped areas or diffraction zones of the lens.

The ring-shaped first diffraction zones of the first lens region may all be formed on the front side or may all be formed on the back side. However, first diffraction zones may also be situated both on the front side and on the back side.

The first lens region has a plurality of first diffraction zones. This means that at least two first diffraction zones are present. If light at a wavelength λ is incident on the at least two diffraction zones then there can be an interference of the light between these diffraction zones. In this case, constructive interference may occur if a phase shift of a multiple of the wavelength λ□ occurs between the diffraction zones; these are the orders of diffraction. A positive order of diffraction is present if the difference of the optical path lengths between a diffraction zone arranged further to the outside and a diffraction zone arranged further to the inside is positive. A respective refractive power can be assigned to the various orders of diffraction on account of the ring-shaped arrangement of the diffraction zones about the principal optical axis. The area or size of the diffraction zones determine the distances between the orders of diffraction and hence the distances between the refractive powers of the lens. In this case, these distances become larger as the area of the diffraction zones decreases. The diffraction zones produce additive refractive powers relative to the refractive power of the basic form of the diffractive lens.

The principal sub-zone—or else echellette zone—of each first diffraction zone typically has a curvature—i.e., a second spatial derivative of the boundary surface that differs from zero. The curvature is preferably constant and the principal sub-zone for example has a spherical form. The curvature may also vary spatially: by way of example, the principal sub-zone has an aspherical form. A principal sub-zone always has a continuous (steady) curvature. The phrase phase sub-zone comprises regions of the diffraction zones which deviate from the continuous (steady) curvature profile of the principal sub-zone; this also includes influences of tools on the topography. In the height profile a principal sub-zone and a phase sub-zone merge continuously into one another.

However, by definition the curvature is discontinuous in the transition between a principal sub-zone and a phase sub-zone. The gradient may likewise be discontinuous in the transition if the height profile has an edge. This may occur for example in the transition from a phase sub-zone of one diffraction zone to a principal sub-zone of another diffraction zone.

The object of the phase sub-zone is to produce an optical path length difference between two principal sub-zones. This means that the phase sub-zones and the principal sub-zones are designed such that an optical path length difference t is produced between the principal sub-zones of two adjacent diffraction zones. The optical path length difference is consequently linked to the profile depth of the phase sub-zone (extent in the direction of the principal optical axis) and the refractive indices upstream and downstream of the boundary surface. The optical path length difference t determines the relative maximum intensities in the individual orders of diffraction (or the assigned additive refractive powers). By way of example, if the phase shift is half a wavelength ($t=\lambda/2$), maximum intensities of $(2/\pi)^2=40.5\%$ for the zeroth and +1st order of diffraction arise for regular, zone plate profiles. In this case, 100% correspond to the maximum intensity of a diffraction-limited “normal” refractive lens (of the same refractive power and with the same diameter). By way of example, for regular zone plate profiles the refractive power of the zeroth order of diffraction dominates for phase shifts whose absolute value is less than half a wavelength λ. The refractive power of the +1st order of diffraction has the greatest relative intensity if the optical path length difference is greater than half a wavelength and less than three half wavelengths ($\lambda/2<t<\lambda\cdot 3/2$). The design of the principal sub-zones and phase sub-zones and the optical path length differences between adjacent principal sub-zones accompanying this consequently determine how much light is directed into which order of diffraction and hence which additive refractive power has how much intensity.

According to example embodiments of the invention, the diffractive optical structure in the first lens region is designed such that for a design wavelength there is a significant diffraction efficiency for optical path length differences between the first principal sub-zones of more than one wavelength λ. In this case, the design wavelength should be understood to mean the light wavelength for which the diffractive eye lens is intended to be optimized: consequently, a sharp image can be produced on the retina for the design wavelength in conjunction with an eye. A significant diffraction efficiency is present for example if at least 8% of the maximum intensity, in another example at least 10% of the maximum intensity and in a further example at least 15% of the maximum intensity of a diffraction limited "normal" refractive lens is obtained for the relevant order of diffraction. According to the invention the diffractive eye lens consequently has a significant intensity for a refractive power which corresponds to an order of diffraction greater than or equal to the first order of diffraction. This advantageously permits a compensation of longitudinal chromatic aberrations.

By way of example, the size or area of a diffraction zone can be determined by virtue of the diffraction zone being projected onto a plane perpendicular to the principal optical axis. The area of the diffraction zone in this projection plane corresponds to the area or size of the diffraction zone. The areas of a principal sub-zone and a phase sub-zone can be defined analogously. A zone size is the umbrella term for the sizes of the diffraction zone, principal sub-zone and phase sub-zone. For an annular zone (i.e., diffraction zone, principal sub-zone or phase sub-zone), the area $A_{zone}$ arises from the difference of the squares of the maximum and minimum radius of the zone multiplied by π:

$$A_{Zone}=\pi\cdot(r_{max,Zone}^2-r_{min,Zone}^2)$$

Consequently, $A_{BZ,i}=\pi\cdot(r_{max,BZ,i}^2-r_{min,BZ,i}^2)$, $A_{HUZ,i}=\pi\cdot(r_{max,HUZ,i}^2-r_{min,HUZ,i}^2)$ and $A_{PUZ,i}=\pi\cdot(r_{max,PUZ,i}^2-r_{min,PUZ,i}^2)$ applies to an i-th diffraction zone (BZ), principal sub-zone (HUZ) and phase sub-zone (PUZ), respectively. In this case, i=1, 2, . . . N applies and Nis the number of zones of the lens region: N≥2 applies. For a circular zone, the minimum radius corresponds to the value of zero in the aforementioned formulas.

The proportion of the area of the first diffraction zones made up by the principal sub-zones can be averaged over all first diffraction zones in the first lens region. By way of example, the average can be formed over a mean value of the relationships of the zone sizes:

$$M=\frac{1}{N}\cdot\sum_{i=1}^{N}\frac{A_{HUZ,i}}{A_{BZ,i}}$$

Optical simulations have shown that there is a causal link between the intensity of the secondary halo ("deep halo") and the proportion of the area of the diffraction zones made up by the principal sub-zones. The proportion of light that can be assigned to each optical power was calculated. To this end, use was made of an algorithm which calculates the diffraction efficiency for any defocus positions according to the Fraunhofer diffraction integral. It was found that numerically large negative orders of diffraction of a diffractive eye lens are to be assigned to a negative blaze angle and the Fourier transform of the phase sub-zones. In turn, refractive powers can be assigned to the negative orders of diffraction. Surprisingly, these (negative) refractive powers are of the same order of magnitude as the (positive) refractive contribution of an eye with an implanted diffractive eye lens (also referred to as "implanted eye"). Consequently, the negative addition refractive powers of the extraneous light are largely compensated by the refractive power of the cornea and the refractive power for the distance focus of the diffractive eye lens.

This has as a consequence an unfocused, relatively large low intensity circle of confusion on the retina. On account of the logarithmic retinal brightness sensitivity, the latter is perceived as a secondary halo. Surprisingly, it is consequently the low intensities at high negative orders of refraction that are responsible for this disruptive effect. By reducing the proportions of the area of the diffraction zones made up by the phase sub-zones the efficiency in the high negative orders of diffraction is reduced. Therefore, the first lens region is designed in such a way according to the invention that averaged over all diffraction zones the principal sub-zones make up a proportion of the diffraction zones of at least 94%, for example at least 95%.

The production method of the diffractive eye lens must be adapted to obtain such a value of the proportion of the area of the principal sub-zones (or phase sub-zones) making up the diffraction zones. In particular, the employed tool must be chosen accordingly. Typically, the diffractive optical structure of a diffractive eye lens is produced in a turning process. In this case, a diamond tool moves relative to a rotating diffractive eye lens blank and in the process removes material from the eye lens blank for the purposes of producing the eye lens. The greater the radius of the diamond tool, the more material can be removed from the eye lens at the same time (or per rotation of the eye lens blank). The smaller the radius of the diamond tool, the less material can be removed from the eye lens at the same time (or per rotation of the eye lens blank). From this, more rotations are required to produce a diffractive eye lens using a tool with a small radius compared to using a tool with a large radius. However, using a diamond tool with a large tool radius sets an upper limit of the proportion of the area made up of the principal sub-zones, said limit arising from the geometry or the topography or the height profile of the diffraction zone (or principal sub-zone and phase sub-zone). Since the phase sub-zone comprise the regions of the diffraction zones which deviate from the continuous (constant) curvature profile of the principal sub-zone, influences of tools on the topography are also included in that case. Consequently, the choice of the tool radius is linked to the size of a phase sub-zone.

Optical simulations have shown that an increase of the proportion of the principal sub-zones making up the diffraction zones from 89% to 94% leads to the integral diffraction efficiency of the negative orders of diffraction reducing by more than 50%. The secondary halo is reduced in this manner.

The diffractive eye lens according to the invention consequently facilitates an improvement in the visual properties of the eye lens by reducing the halo.

According to an example configuration of the diffractive eye lens, the diffractive structure comprises at least one second lens region with a second ring-shaped diffraction zone circumferential the principal optical axis of the eye lens. This may be an individual second diffraction zone or else a plurality of second diffraction zones. Each second diffraction zone has a further principal sub-zone and a further phase sub-zone. Furthermore, averaged over all second diffraction zones the further principal sub-zones make up a proportion of the second diffraction zones of for example at least 94%, in a further example at least 95% for the second lens region. Finally, the first lens region and the second lens region differ from one another in at least one of the following optical parameters: an optical path length difference, a zone size.

The second lens region (or even further lens regions) can be situated on the same side or on the opposite side of the diffractive eye lens as the first lens region. Additionally, both lens regions (or even further lens regions) can be arranged on both sides of the eye lens in each case.

What is ensured as a result of the proportion of the further principal sub-zones making up at least 94% of the second diffraction zones—averaged over all second diffraction zones—is that the visual properties of the eye lens are improved by reducing the halo for the at least one second lens region as well.

The aforementioned optical parameters of the lens regions allow influencing of the diffraction efficiency and the additive refractive power. Consequently, using more than one lens region advantageously allows further foci to be produced by the diffractive eye lens.

In an example embodiment of the diffractive eye lens with at least two lens regions, the first lens region has at least two first diffraction zones, between which at least one second diffraction zone of the second lens region is arranged when viewed in the radial direction around the principal optical axis. In particular, the first diffraction zones and the second diffraction zones are arranged in alternating sequence when viewed in the radial direction.

If the diffractive eye lens has more than two lens regions, at least one diffraction zone of each further lens region can be situated between the at least two first diffraction zones in the radial direction.

What the arrangement described advantageously ensures is that the optical powers of the two (or more) lens regions can be obtained for variable pupil diameters of the eye. By way of example, if the pupil contracts in bright ambient light and consequently only has a small diameter, diffraction zones of all lens regions can still be situated within this diameter. The same applies to dark ambient light with a large pupil of the eye. In this way, the optical power of the diffractive eye lens advantageously remains independent of the adaptation of the eye.

In an example embodiment of the diffractive eye lens, the respective principal sub-zone makes up the proportion of the respective diffraction zone of at least 94% for all of the first diffraction zones. If the diffractive eye lens has a second lens region, the respective principal sub-zone additionally or alternatively makes up the proportion of the respective diffraction zone of at least 94% for all of the second diffraction zones. Expressed differently, this means that the component is $A_{HUZ,i}/A_{Bz,i} \geq 94\%$ for all i=1, 2, . . . N of the N first and/or second diffraction zones of the first and/or second lens region. Preferably, the respective proportion is at least 95% in each case.

A diffractive eye lens designed thus has a further reduced secondary halo since the diffraction of light into negative orders of diffraction is additionally reduced.

According to a further example embodiment of the diffractive eye lens, the diffractive optical structure is designed in such a way in the first lens region and/or in the second lens region that at the design wavelength there is no significant diffraction efficiency in negative orders of diffraction. For example, there is no significant diffraction efficiency in orders of diffraction less than or equal to zero. This means that there are no significant diffraction efficiencies in all orders of diffraction smaller than the +1st order of diffraction.

Thus, the diffractive eye lens for example is a pure diffraction lens since the zeroth order of diffraction has only a small intensity. In this case, the term "no significant diffraction efficiency" or "non-significant diffraction efficiency" should be understood for example to mean that at most 8% of the maximum intensity, in a further example at most 5% of the maximum intensity and in another example at most 1% of the maximum intensity of a diffraction limited "normal" refractive lens is obtained for the relevant order of diffraction. There can be an intermediate range in which the diffraction efficiency is neither significant nor non-significant between a significant diffraction efficiency, as defined further above, and a non-significant diffraction efficiency defined here.

As a result of the property that the diffractive eye lens has no significant diffraction efficiency for negative orders of diffraction or the zeroth order of diffraction, it is possible to reduce by way of compensation the overall longitudinal chromatic aberration of the combination of eye lens, cornea and refractive media. Predominant refractive powers with a diffraction efficiency beyond a non-significant diffraction efficiency occur at orders of diffraction greater than or equal to, or greater than, zero. What is consequently ensured is that no longitudinal chromatic aberration caused by negative orders of diffraction amplifies the natural longitudinal chromatic aberration of the eye and consequently leads to perceptible deterioration in contrast in the case of polychromatic illumination. Rather, only the +1st order of diffraction may have a significant diffraction efficiency for example (in addition to a further, higher order of diffraction). In this way, the diffractive eye lens facilitates a correction of the chromatic aberrations of the eye since the longitudinal chromatic aberration thereof in a positive order of diffraction can reduce or even fully compensate the natural chromatic longitudinal aberration of the eye. In this way, a contrast deterioration perceptible to the patient in the case of polychromatic illumination can be reduced.

In an example embodiment, the diffractive eye lens is designed such that at the design wavelength there is a significant diffraction efficiency for at least for example two orders of diffraction, in particular for example for at least three orders of diffraction.

In this way it is possible to realize bifocal, trifocal (or multifocal) eye lenses. It is particularly advantageous for example if additionally, there is no significant diffraction efficiency for negative orders of diffraction or orders of diffraction less than or equal to zero. In this case, this relates to a bifocal (trifocal, multifocal) eye lens which at the same time facilitates a reduction in longitudinal chromatic aberrations. In this case, the distance focus can be assigned to the lowest order of diffraction with a significant diffraction efficiency—for example the +1st order of diffraction.

The diffractive eye lens according to the invention consequently facilitates the reduction of the halo while simultaneously providing a plurality of focal positions as a bifocal, trifocal of multifocal lens.

According to a further example configuration, the diffractive eye lens is distinguished in that a maximum diffraction efficiency is for example less than 0.3%, in another example less than 0.15% in a defocus range. In this case, the defocus range ranges for example at least from −45 dpt to −15 dpt with respect to the refractive power of the distance focus, in another example at least from −60 dpt to −10 dpt.

The smallest refractive power with a significant diffraction efficiency can be assigned to the distance focus. Light guided with even lower additive refractive powers can never be imaged sharply on the retina: it is imaged in defocused fashion. This range of the refractive powers is referred to as the defocus range. By way of example, if the distance focus has an additive refractive power of +2 dpt (with respect to the refractive power of the basic form of the diffractive eye lens), the defocus range ranges for example at least from −43 dpt additive refractive power to −13 dpt additive refractive power, in another example at least from −58 dpt additive refractive power to −8 dpt additive refractive power.

In particular, the secondary halo is caused by the light guided with such (low) refractive powers in the direction of the retina which just compensate the refractive power of the implanted eye: the positive contribution of the implanted eye (in particular of the cornea) is of the same order of magnitude as the negative contribution by a negative refractive power (by the diffractive eye lens).

To reduce or even avoid the secondary halo, the diffraction efficiency in the defocus range must not exceed a limit. The limit may be the above-described maximum diffraction efficiency occurring in the defocus range.

According to a further example configuration, the diffractive eye lens is distinguished in that an integrated diffraction efficiency is for example less than 6%, in another example less than 2% in a defocus range. In this case, the defocus range ranges at least from for example −45 dpt to −15 dpt with respect to the refractive power of the distance focus, in another example at least from −60 dpt to −10 dpt. The aforementioned limits thus relate the diffraction efficiencies integrated over the defocus range to the diffraction efficiencies integrated over all occurring additive refractive powers.

According to the invention, the introduced maximum and integral limits for the defocus range ensure that a secondary halo as a result of the diffractive eye lens is reduced even when taking account of the logarithmic retinal brightness sensitivity. Particularly advantageously, both the limits for the maximum diffraction efficiency and the integrated diffraction efficiency are observed to this end within the defocus range for example.

In a further example embodiment of the diffractive eye lens, the design wavelength is in a central spectral range of a luminous efficiency function. For example, the design wavelength is between 530 nm and 570 nm, for example at 550 nm or at 546 nm.

The luminous efficiency function describes the sensitivity of the human eye as a function of the wavelength of the light. For example, use is made of the photopic luminous efficiency function (daytime vision). Alternatively, use can be made of a mesopic luminous efficiency function (twilight vision) or scotopic luminous efficiency function (night vision). A central spectral range of the luminous efficiency function should be understood to mean those wavelengths for which the brightness sensitivity is at least 30%, for example at least 50%, in another example at least 70% of the maximum brightness sensitivity.

A design wavelength of between 530 nm and 570 nm is particularly advantageous for example since the brightness sensitivity in daylight is more than 80% in this case. More than 99% and 98% are achieved for a design wavelength of 550 nm and 546 nm, respectively. Thus, the use of a design wavelength chosen thus is suitable for daylight in particular.

The optimization of the diffractive eye lens for a design wavelength corresponding to the specifications above advantageously leads to the refractive power (or the refractive powers in the case of a bifocal or multifocal eye lens) being optimized in accordance with high spectral brightness sensitivity of the eye. Additionally, the secondary halo is reduced particularly efficiently for those wavelengths to which the human eye is sensitive. This leads to a further improvement in the visual properties of the eye lens under routine ambient conditions.

According to a further example embodiment of the diffractive eye lens, all diffraction zones of a lens region have the same zone size. Additionally or alternatively, all diffraction zones of a lens region have the same optical path length difference.

If the eye lens comprises more than one lens region, the diffraction zones of the respective lens region therefore have the same zone size or the same optical path length differences. However, the zone size or the optical path length difference of the first lens region can deviate from the zone size or from the optical path length difference of a further lens region.

In a further example embodiment, the diffractive eye lens is produced from a biocompatible material and suitable for implantation in the eye.

The use of a biocompatible material ensures there cannot be a rejection reaction of the eye when the diffractive eye lens is implanted into an eye.

According to a further embodiment, the diffractive eye lens is a contact lens, an intraocular lens or an intracorneal lens.

A second aspect of the invention relates to a method for producing a diffractive eye lens according to any one of the above-described embodiments. As already discussed above, the size of the tool used when producing the diffractive eye lens influences the proportion of the area that a principal sub-zone can make up in a diffraction zone. If the tool radius is too large, it is not possible to manufacture the required proportion p of 94% to 95%. For the phase sub-zone (PUZ) of an i-th diffraction zone (BZ) which adjoins the principal sub-zone (HUZ) when viewed in the radial direction around the principal optical axis, the width of the phase sub-zone is given by $\delta_i = r_{max,PUZ,i} - r_{min,PUZ,i} = r_{max,PUZ,i} - r_{max,HUZ,i}$. The width of the i-th diffraction zone is $\Delta_i = r_{max,PUZ,i} - r_{min,HUZ,i}$. For the required proportion p of area of the i-th diffraction zone, the following applies:

$$\frac{\pi \cdot (r_{max,HUZ,i}^2 - r_{min,HUZ,i}^2)}{\pi \cdot (r_{max,PUZ,i}^2 - r_{min,HUZ,i}^2)} \geq p$$

From this, the following follows for the proportion of the area of the diffraction zone made up by the phase sub-zone:

$$\frac{\pi \cdot (r_{max,PUZ,i}^2 - r_{max,HUZ,i}^2)}{\pi \cdot (r_{max,PUZ,i}^2 - r_{min,HUZ,i}^2)} \leq 1 - p$$

This expression can be rewritten as:

$$\frac{(r_{max,PUZ,i} - r_{max,HUZ,i})}{(r_{max,PUZ,i} - r_{min,HUZ,i})} \cdot \frac{(r_{max,PUZ,i} + r_{max,HUZ,i})}{(r_{max,PUZ,i} + r_{min,HUZ,i})} \leq 1 - p$$

In this case, the first factor corresponds precisely to the proportion of the width of the diffraction zone $\Delta_i$ made up by the width of the phase sub-zone $\delta_i$. The second factor is always greater than 1 since $r_{max,HUZ,i} > r_{min,HUZ,i}$ applies. Thus $\delta_i/\Delta_i \leq 1-p$ emerges.

The width of the phase sub-zone $\delta_i$ can typically be no less than the radius of the tool used to produce the i-th diffraction zone.

The method according to the invention for producing a diffractive eye lens comprises the method step of providing an eye lens blank. Further, the method comprises the step of ablating material of the eye lens blank to produce a diffraction zone using a tool. A turning method is typically used for processing. In this case, a tool moves relative to the eye lens blank and, in the process, removes material from the eye lens blank; the eye lens blank typically rotates in the process. According to the invention, the employed tool has a radius which corresponds to at most 6%, for example at most 5% of the width of the diffraction zone.

This ensures that the tool used (intermittently, for producing the diffraction zone) is suitable for manufacturing the required proportion of 94% (or 95%) of the area of the diffraction zone made up by the principal sub-zone. Tools with other radii can be used to manufacture other parts of the diffractive eye lens. Thus, a tool can be changed during the manufacture of the diffractive eye lens.

For example, material for producing each diffraction zone is removed using a tool which satisfies the demands regarding a maximum radius of the corresponding diffraction zone.

The absolute width of a phase sub-zone decreases with increasing radial distance between the diffraction zone and the principal optical axis. To be able to manufacture the diffractive structure of a diffractive eye lens using only one tool, material to produce all diffraction zones is removed using a tool having a radius that for example corresponds to no more than 6% (or 5%) of the width of the outermost diffraction zone as viewed in the radial direction around the principal optical axis (A).

It is understood that the features mentioned above and the features still to be explained below can be used not only in the specified combinations but also in other combinations or on their own without departing from the scope of the present invention.

BRIEF DESCRIPTION OF THE DRAWINGS

The invention is explained in greater detail below for example with reference to the accompanying drawings, which also disclose features essential to the invention. In the drawings.

DETAILED DESCRIPTION

Figure 1A:
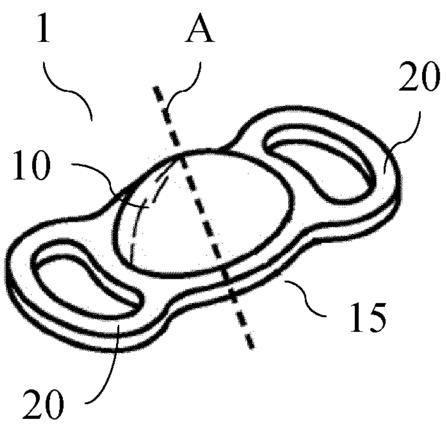
FIG. 1*a* depicts a perspective illustration of a first example embodiment of a diffractive eye lens according to the invention.

FIG. 1*a* depicts a perspective illustration of a first example embodiment of a diffractive eye lens 1 according to the invention, which is in the form of an intraocular lens (IOL). The eye lens comprises a front side 10 and a back side 15, and also a haptic 20. The eye lens 1 is held in the eye by presence of the haptic 20. The eye lens 1 is foldable and may be introduced into an eye through a small incision. The front side 10 and the back side 15 are responsible for the optical imaging properties of the eye lens 1. A principal optical axis A is perpendicular to an imaginary plane situated between the front side 10 and the back side 15 of the eye lens 1. In the implanted state of the eye lens 1 in the eye, the example front side 10 faces the cornea, whereas the back side 15 faces away from this cornea.

Figure 1B:
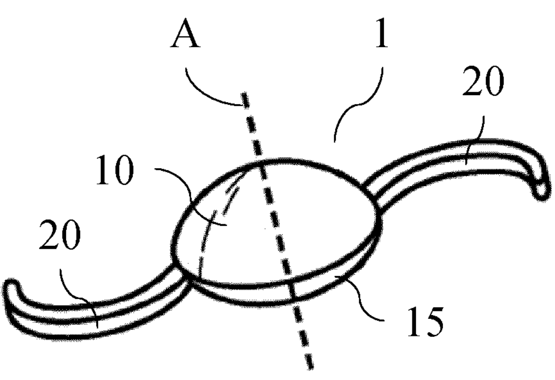
FIG. 1*b* depicts a perspective illustration of a further example embodiment of a diffractive eye lens according to the invention.

FIG. 1*b* depicts a perspective illustration of a further example embodiment of a diffractive eye lens 1 formed as an intraocular lens. Said lens differs from the embodiment in FIG. 1*a* by way of having a different haptic 20.

In principle, differently shaped and configured haptics 20 may also be provided.

Figure 2:
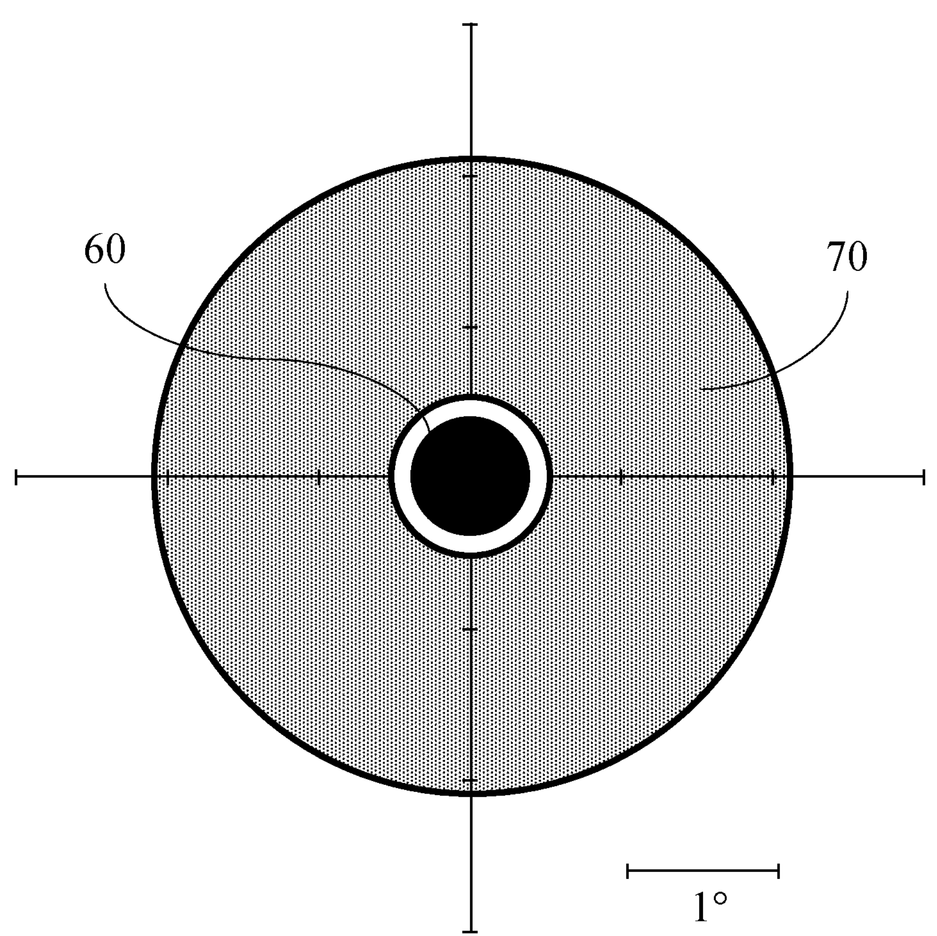
FIG. 2 depicts a schematic illustration of the halo for a diffractive eye lens.

FIG. 2 is a schematic illustration of the halos for a diffractive, multifocal eye lens 1. Depicted is the light distribution produced by a punctiform light source on a retina of the eye in which a diffractive eye lens 1 has been implanted. In this case, the punctiform light source is at a distance and the eye lens 1 is designed such that the implanted eye is corrected for distance. The image of the punctiform light source on the retina is assigned to the horizontal and vertical coordinate (0°, 0°). This picture element on the retina is surrounded by a primary halo 60, which in the schematic illustration has a diameter of approximately 1° (object angle). The cause for the unavoidable primary halo lies in the simultaneous superpositions of the foci of the utilized orders of diffraction. In the radial direction (to larger object angles in the horizontal and vertical direction), the primary halo 60 is adjoined by a further stray light zone, which is referred to as secondary halo 70. The cause for the secondary halo 70 lies in unused and consequently unwanted orders of diffraction of the diffractive eye lens 1. In the illustrated example, the secondary halo 70 extends in the radial direction to object angles of slightly more than 2°. Light contributing to the secondary halo 70 may also be diffracted to locations on the retina where the primary halo 60 is situated. However, the primary halo 60 outshines this light.

Figure 3:
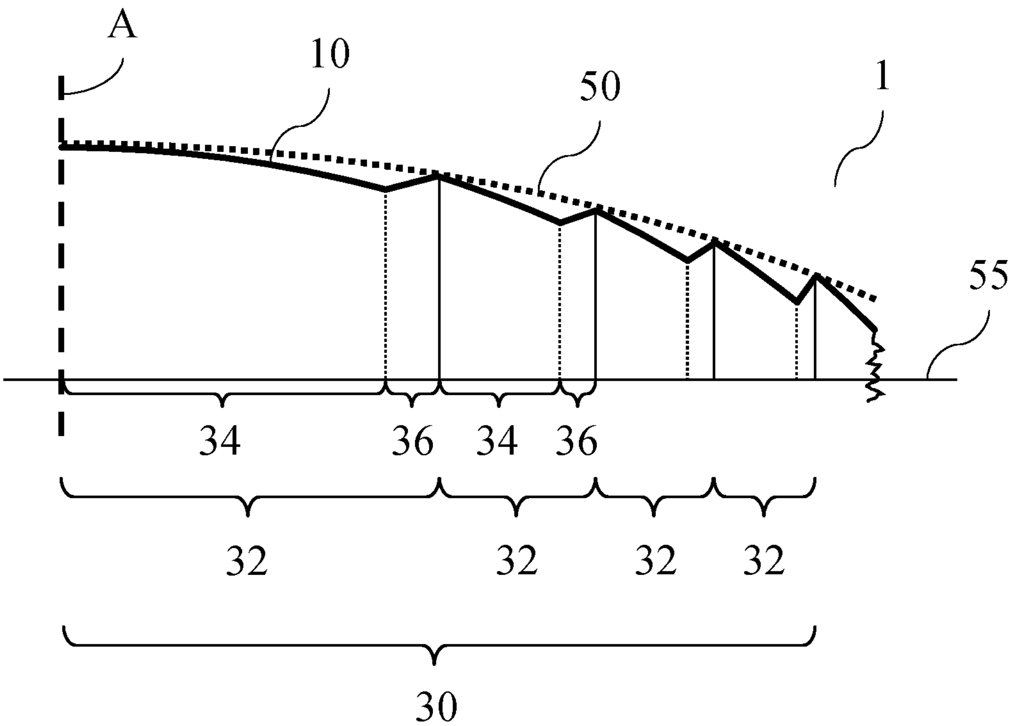
FIG. 3 depicts a schematic illustration of a portion of a lens cross section of a diffractive eye lens according to a further example embodiment.

FIG. 3 is a schematic illustration of a portion of a lens cross section of a diffractive eye lens 1 according to a further example embodiment. The shown sectional plane contains the principal optical axis A and depicts a portion of the profile of the front side 10 of the diffractive eye lens 1. In this case, the eye lens 1 has a first lens region 30. The latter comprises four diffraction zones 32 in the example shown.

These diffraction zones 32 are arranged with rotational symmetry around the principal optical axis A. Each diffraction zone 32 comprises a principal sub-zone 34 and a phase sub-zone 36. All principal sub-zones 34 have the same curvature in the illustrated example. Alternatively, the principal sub-zones may also have different curvatures. Phase sub-zones 36 are arranged between the principal sub-zones 34. Their curvature deviates from the curvature of the respective principle sub-zones 34. The transitions between principal sub-zones 34 and phase sub-zones 36 of a diffraction zone 32 have discontinuous curvatures. The object of the phase sub-zones is to produce for a design wavelength an optical path length difference between the respective principal sub-zones 34.

The size or area of the individual diffraction zones 32, principal sub-zones 34 and phase sub-zones 36 emerges from the projection onto a plane perpendicular to the principal optical axis A. The latter is plotted in FIG. 3 as a line with the reference sign 55. The radial extent (minimum radius and maximum radius) of the zones can be read on the projection plane 55 and can be converted into an area. According to the invention, the proportion of the diffraction zones 32 made up by the principal sub-zone 34 is at least 94%. It should be noted that the depicted proportion of the area of the diffraction zones 32 made up by the principal sub-zones 34 is smaller to make the definition of the various zones clearer.

The basic form 50 of the front side 10 of the diffractive eye lens 1 is plotted as a dotted line. In the example shown, the latter corresponds to the imagined connection between the local maxima in the height profile of the diffractive optical structure.

Figure 4:
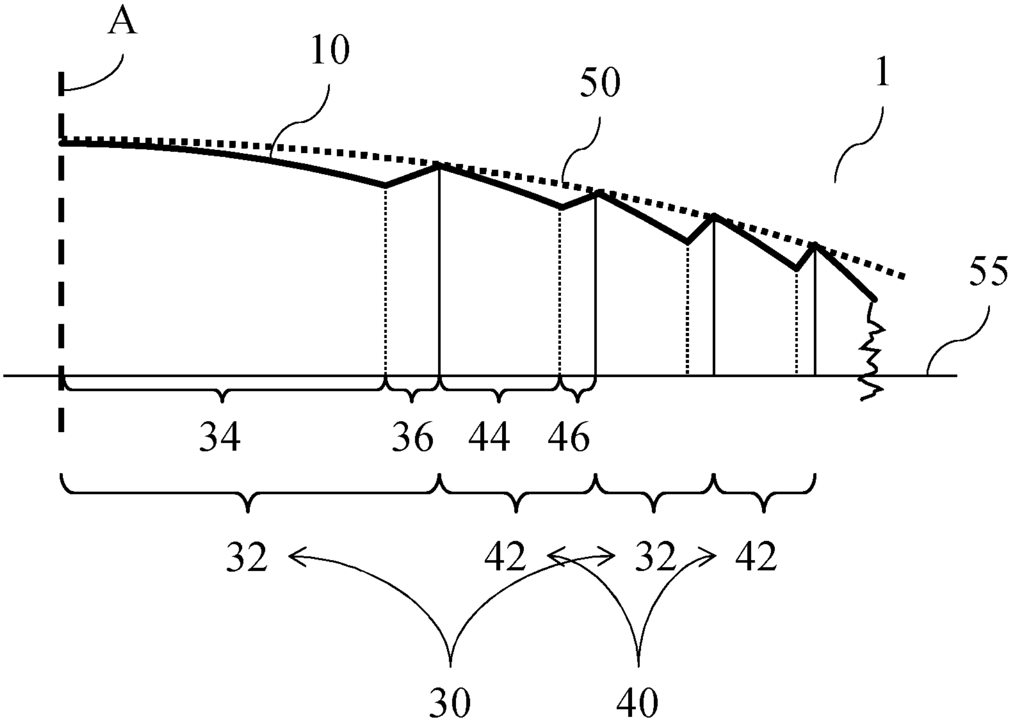
FIG. 4 depicts a schematic illustration of a portion of a lens cross section of a diffractive eye lens according to a further example embodiment with two lens regions.

FIG. 4 is a schematic illustration of a portion of a lens cross section of a diffractive eye lens according to a further example embodiment with two lens regions 30, 40. In this case, the first lens region 30 has two first diffraction zones 32. These each comprise a principal sub-zone 34 and a phase sub-zone 36. The second lens region 40 has two second diffraction zones 42. These likewise each comprise a principal sub-zone 44 and a phase sub-zone 46. The lens regions 30, 40 are arranged on the front side 10 of the diffractive eye lens 1. The first diffraction zones 32 and second diffraction zones 42 alternate in the radial direction with respect to the principal optical axis A. In the example shown, the lens regions 30, 40 have optical path length differences. Alternatively or in addition, the two lens regions 30, 40 may also have different zone sizes. This facilitates additional focal positions for a multifocal, diffractive eye lens 1.

Figure 5A:
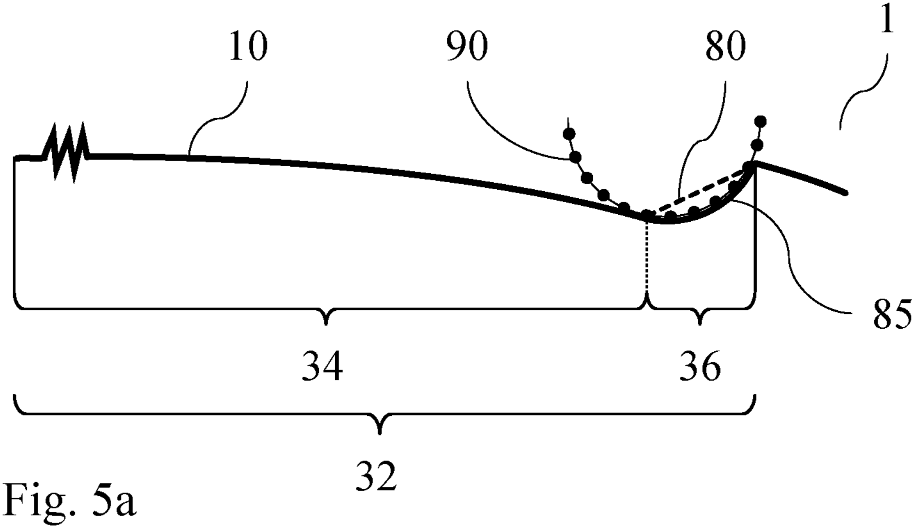
FIGS. 5*a* to 5*c* depict schematic illustrations of a portion of a lens cross section of a diffractive eye lens taking account of different sizes of tools used in the manufacture.

FIG. 5*a* is a schematic illustration of a portion of the front side 10 of a lens cross section of a diffractive eye lens 1 taking account of a diamond tool 90 used in the manufacture. Shown is the portion for a diffraction zone 32 for a radial section like in FIG. 3. Here, too, the diffraction zone 32 comprises a principal sub-zone 34 and a phase sub-zone 36. The principal sub-zone 34 has a curvature. The phase sub-zone 36 comprises all regions of the diffraction zone 32 that deviate from the continuous (constant) curvature profile of the principal sub-zone 34. If the front side 10 were to be processed using an ideal tool with a vanishingly small tool radius, it would be possible to produce a phase sub-zone 36 with an ideal form 80, as plotted by the dashed line in FIG. 5*a*. Then—as plotted—the ideal form 80 could have no roundings. Since the production of an eye lens 1 requires very many rotations of the lens blank if a very small tool is used, use is made of a tool 90 with a finite radius. The profile of the tool 90 is plotted as a line made of dots and dashes. The tool radius yields a real form 85 of the phase sub-zone 36, which is plotted as a solid line.

Figure 5B:
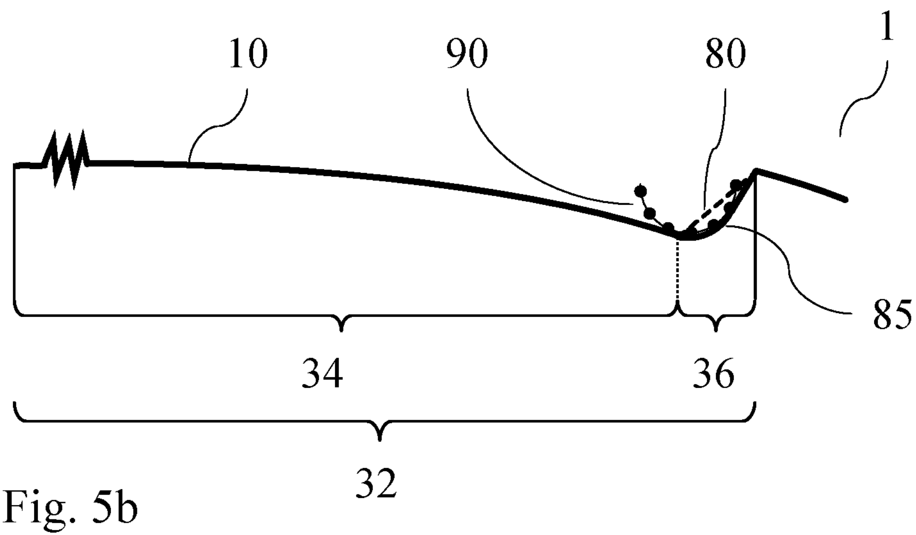

It should be observed that smaller radii of the diamond tool 90 also allow the manufacture of small phase sub-zones 36. By way of example, if the profile depth of a phase sub-zone to be manufactured is greater than the width of the phase sub-zone, the radius of the tool generally limits how small the width of the phase sub-zone can be. This is shown in FIG. 5*b*. The diamond tool 90 used here has a tool radius half the size of the diamond tool 90 used in FIG. 5*a*. In this case, the phase sub-zone can be significantly smaller than in the example according to FIG. 5*a*. A larger number of revolutions of the lens blank might be required to produce the diffraction zone when a diamond tool 90 with a smaller tool radius is used.

Figure 5C:
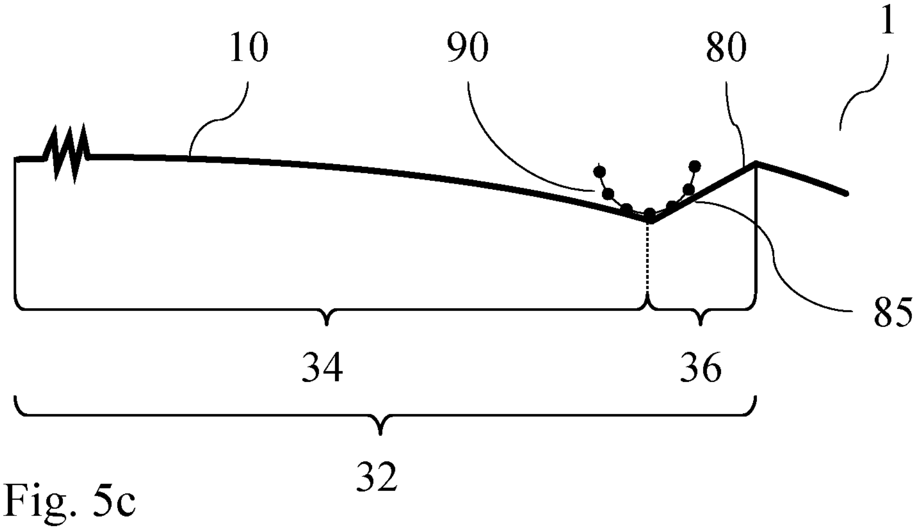

FIG. 5*c* is a schematic illustration of a portion of the front side 10 of a lens cross section of a further diffractive eye lens 1. In this example, the phase sub-zone 36 has exactly the same size as the phase sub-zone 36 from FIG. 5*a*. However, on account of the smaller radius of the diamond tool 90 used here, it is possible for the real phase sub-zone 85 to (almost) correspond to the ideal phase sub-zone 80 of FIG. 5*a*. Since not only the phase shift t produced by the phase sub-zones 36 but also the form of the phase sub-zone 36 influences the diffraction efficiency, taking account of the influence of the radius of the diamond tool 90 is particularly important when producing a diffractive eye lens 1.

Figure 6:
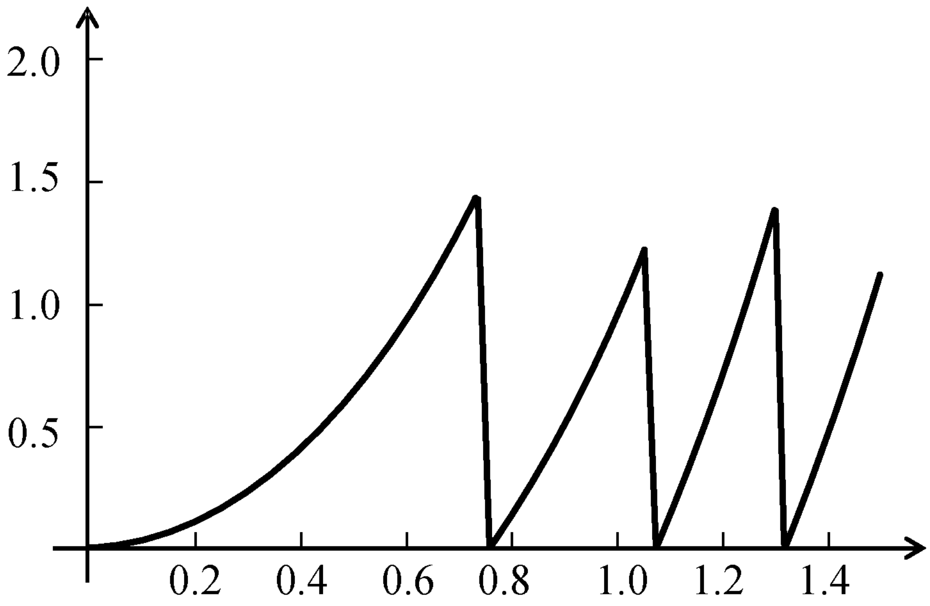
FIG. 6 depicts a diagram for the simulated radial curve of the phase profile of a trifocal, diffractive eye lens.

FIG. 6 is a diagram for the simulated radial curve of the phase profile of a trifocal, diffractive eye lens 1 embodied as an IOL, as produced by the diffractive optical structure. The diagram depicts the effect of an example embodiment with two lens regions 30, 40 and four diffraction zones 32, 42 which are arranged with rotational symmetry about the principal optical axis A. The horizontal axis plots the distance from the principle optical axis A in mm. The first first diffraction zone 32 of the first lens region 30 extends up to a radius of approximately 0.75 mm, the first second diffraction zone 42 of the second lens region 40 extends from approximately 0.75 mm to approximately 1.08 mm and the second first diffraction zone 32 of the first lens region 30 extends from approximately 1.08 mm to approximately 1.32 mm. The second second diffraction zone 42 of the second lens region 40 adjoins the second first diffraction zone 32. The simulations have been carried out for a radius of an eye pupil of 1.5 mm. The second second diffraction zone 42 extends beyond this radius. The vertical axis plots the phase shift in multiples of the design wavelength $\lambda$. At their respective outer edge, the first three diffraction zones 32, 42 produce a phase shift of approximately $1.4\lambda$ or approximately $1.2\lambda$. On account of the curvature of the principal sub-zones 34, 44 of the diffraction zones 32, 42, the radial curve of the phase shift likewise exhibits piecewise curvatures. The sections between the curved portions are to be assigned to the phase sub-zones 36, 46. In the example embodiment shown, the proportion of the diffraction zones 32, 42 made up by the principal sub-zones 34, 44 is respectively 94% for all four diffraction zones 32, 42. What was taken into account in the size of the phase sub-zones 36, 46 and the simulations of the phase shift is that the profile of the diffractive eye lens 1 was produced using a diamond tool 90 having a tool radius that is smaller than the width of the second first phase sub-zone 36.

Figure 7:
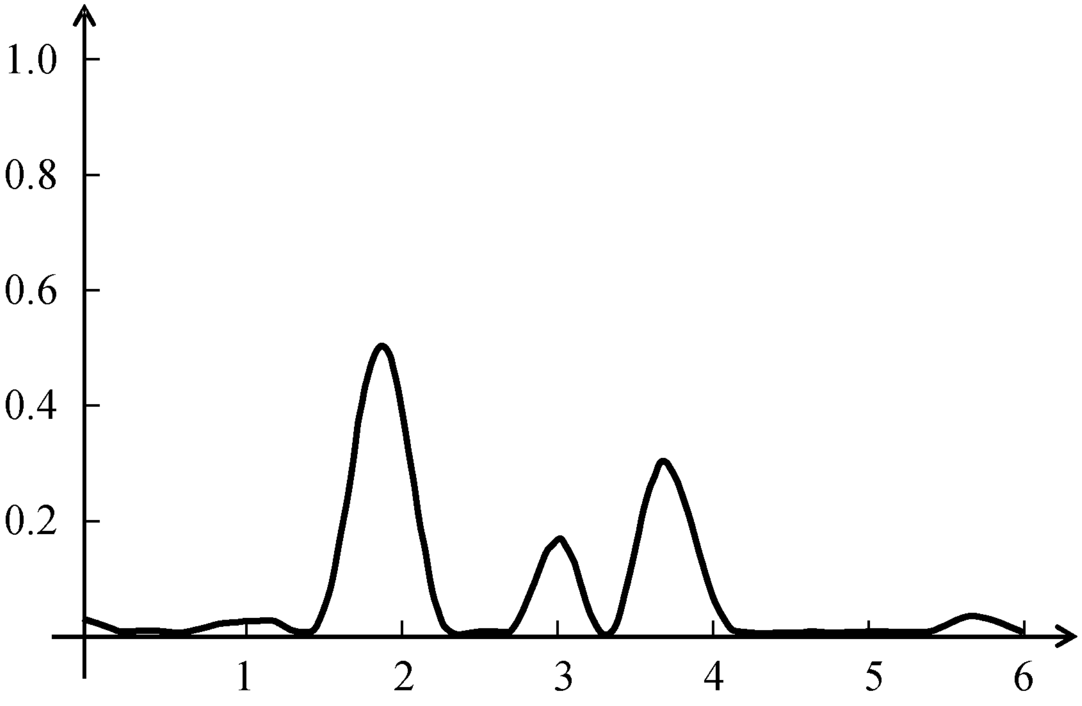
FIG. 7 depicts a diagram for the simulated diffraction efficiency as a function of an additive refractive power in a used range for a trifocal, diffractive eye lens.

FIG. 7 depicts a diagram for the simulated diffraction efficiency as a function of an additive refractive power (with respect to the refractive power of the basic form of the diffractive eye lens) in a used range for a trifocal, diffractive eye lens 1 according to the example embodiment discussed in FIG. 6. In this case, the used range comprises the range of the additive refractive powers in which there is a significant diffraction efficiency. In the diagram, the additive refractive power is plotted along the horizontal axis in diopter (dpt). The diffraction efficiency is plotted on the vertical axis. In this case, the value 1 corresponds to the maximum intensity of a diffraction limited "normal" refractive lens (of the same refractive power and with the same diameter). In this example embodiment, the first maximum of the diffraction efficiency occurs at an additive refractive power of approximately 1.85 dpt, with an efficiency of approximately 0.5. This is to be assigned to the distance focus: approximately 50% diffraction efficiency is assigned to the latter. A further maximum occurs at an additive refractive power of approximately 3 dpt and has a diffraction efficiency of approximately 0.16 (approximately 16% diffraction efficiency); this diffraction maximum assists vision at a mid distance (intermediate vision). A third maximum occurs at an additive refractive power of approximately 3.7 dpt and has a diffraction efficiency of approximately 0.33 (approximately 33% diffraction efficiency); this diffraction maximum assists vision at shorter visual distances. Thus, the example embodiment shown is a trifocal, diffractive eye lens 1. In this case, there is no significant diffraction efficiency in the zeroth order of diffraction at an additive refractive power of 0 dpt. The diffractive eye lens 1 is what is known as a multi-order phase plate (MOD optical unit). The depicted example embodiment facilitates a correction of the longitudinal chromatic aberrations of the implanted eye even at the distance focus.

Figure 8A:
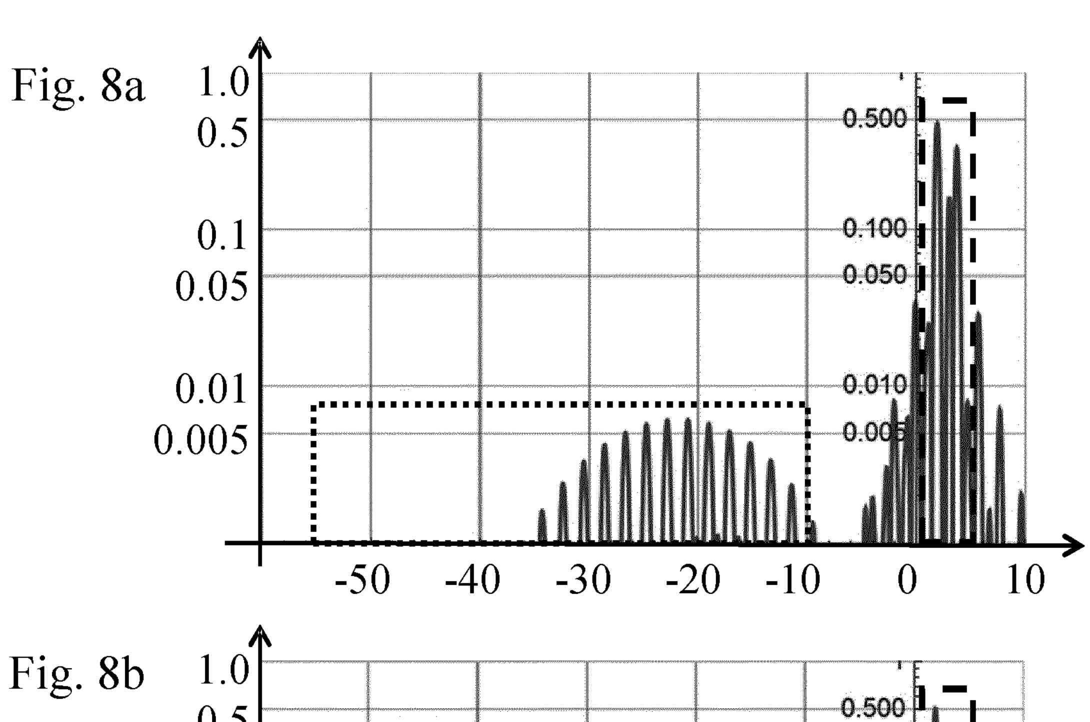
FIG. 8*a* depicts a diagram for the simulated diffraction efficiency as a function of an additive refractive power for a used range and a defocus range for a trifocal, diffractive eye lens according to the prior art.

FIG. 8*a* is a diagram for the simulated diffraction efficiency as a function of an additive refractive power for a used range and a defocus range for a trifocal, diffractive eye lens according to the prior art. Like in FIG. 7, the horizontal axis also plots the additive refractive power in diopter. However, this depicts a section from −60 dpt to +10 dpt. The diffraction efficiency is plotted on the vertical axis. The vertical axis has a logarithmic scale in this case. This also allows the representation of small diffraction efficiencies. The diffraction efficiency as a function of the additive refractive power depicted here corresponds to the properties of a diffractive eye lens, in which the principal sub-zones 34 only make up the proportion of 88% of the diffraction zones 32. The diffraction efficiencies in a used range between 1.5 dpt and 4.5 dpt (approximately) correspond to those illustrated in FIG. 7 for an example embodiment: the corresponding region of the additive refractive powers is marked in FIG. 8*a* using a dashed box. In respect of the used orders of diffraction, the diffractive eye lens according to the prior art shown here therefore behaves (approximately) like an eye lens 1 according to the invention. For a defocus range which is marked here by a dotted box and which extends from −55 dpt to −10 dpt (i.e., from approximately −57 dpt to approximately −12 dpt with respect to the refractive power of the distance focus, which is at approximately 2 dpt), this example according to the prior art however has diffraction efficiencies that are up to 0.6%. Raised diffraction efficiencies occur in particular between −30 dpt and −15 dpt. These negative addition refractive powers of the stray light just largely compensate the refractive power of the cornea and the refractive power for the distance focus of the diffractive eye lens. Consequently, they are noticeable as a secondary halo on account of the logarithmic retinal brightness sensitivity.

If the secondary halo is assessed by way of an integration of the diffraction efficiencies in the defocus range, a value of approximately 8% with respect to the diffraction efficiencies integrated over all occurring additive refractive powers arises in the shown example according to the prior art.

Figure 8B:
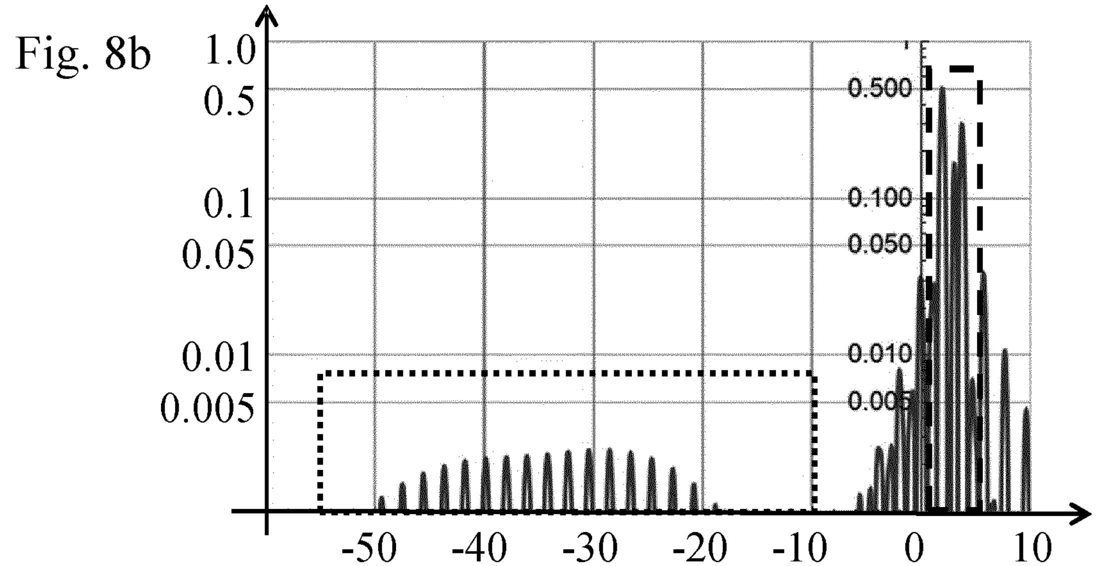
FIG. 8*b* depicts a diagram for the simulated diffraction efficiency as a function of an additive refractive power for a used range and a defocus range for a trifocal, diffractive eye lens according to the invention.

FIG. 8*b* depicts a diagram for the simulated diffraction efficiency as a function of an additive refractive power for a used range and a defocus range for an example embodiment of a trifocal, diffractive eye lens 1 according to the invention. The representations of the horizontal and vertical axes correspond to those in FIG. 8*a*. In this case the diffraction efficiency as a function of the additive refractive power depicted corresponds to the properties of a diffractive eye lens 1, in which the principal sub-zones 34, 44 each make up the proportion of 94% of the diffraction zones 32, 42. The diffraction efficiencies in a used range correspond to those depicted in FIG. 7 for one example embodiment. For a defocus range which is marked here by a dotted box and which extends from −55 dpt to −10 dpt, this example embodiment has diffraction efficiencies that are no more than merely 0.25%. If the secondary halo is assessed by way of an integration of the diffraction efficiencies in the defocus range, a value of only approximately 5% with respect to the diffraction efficiencies integrated over all occurring additive refractive powers arises in the shown example embodiment. Consequently, the secondary halo is significantly reduced by the eye lens according to the invention.

Figure 8C:
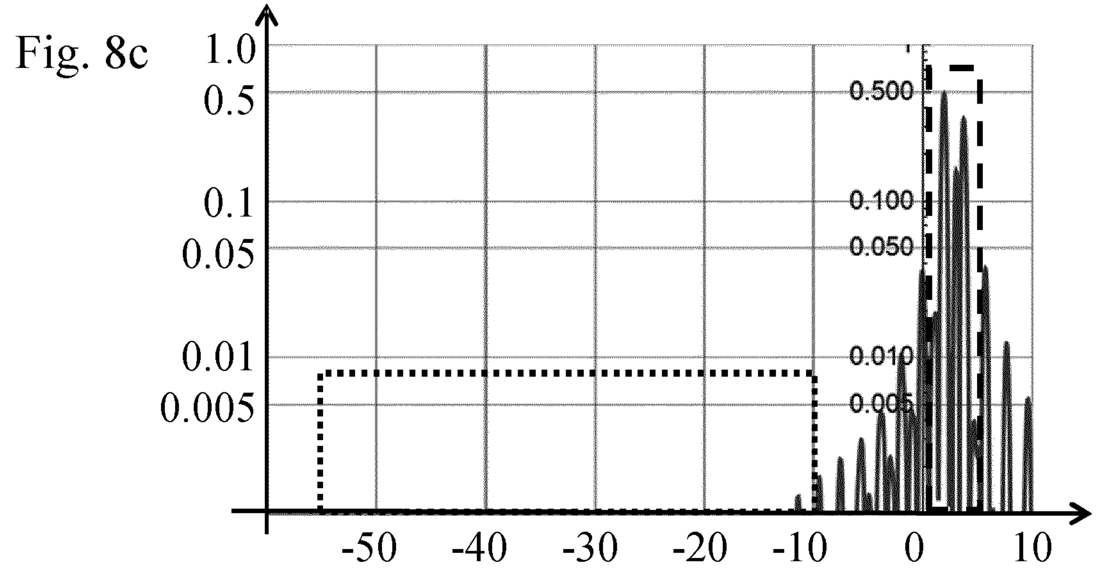
FIG. 8*c* depicts a diagram for the simulated diffraction efficiency as a function of an additive refractive power for a used range and a defocus range for a further trifocal, diffractive eye lens according to the invention.

FIG. 8*c* depicts a diagram for the simulated diffraction efficiency as a function of an additive refractive power for a used range and a defocus range for a further example embodiment of a trifocal, diffractive eye lens 1 according to the invention. In this case the diffraction efficiency as a function of the additive refractive power depicted corresponds to the properties of a diffractive eye lens 1, in which the principal sub-zones 34, 44 each make up the proportion of 98% of the diffraction zones 32, 42. The diffraction efficiencies in the used range again correspond to those depicted in FIG. 7 for one example embodiment. This example embodiment has diffraction efficiencies of less than 0.13% in the defocus range from −55 dpt to −10 dpt. If the secondary halo is assessed by way of an integration of the diffraction efficiencies in the defocus range, a value of only 1.4% with respect to the diffraction efficiencies integrated over all occurring additive refractive powers arises in the shown example embodiment. Consequently, the secondary halo is significantly reduced further by the eye lens according to the invention.

If the intensities of the secondary halo for the described example embodiment according to FIG. 8*c* are considered in a lateral cross section in the retina, this yields a reduction of the retinal intensity of the halo by one order of magnitude compared to the prior art according to FIG. 8*a*.

In this case, the aforementioned features of the invention, which are described in various exemplary embodiments, can be used not only in the specified example combinations but also in other combinations or on their own, without departing from the scope of the present invention.

A description of a piece of equipment relating to method features is analogously applicable to the corresponding method with respect to these features, while method features correspondingly represent functional features of the equipment described.

The invention claimed is:

1. A diffractive eye lens having a front side, a back side and a principal optical axis, wherein the front side, the back side or both have a spherical, an aspherical, a spherical-toroidal, an aspherical-toroidal or a free-form-shaped basic form, and the front side, the back side or both have a diffractive optical structure, the diffractive optical structure comprising a first lens region with a plurality of first ring-shaped diffraction zones circumferential to the principal optical axis of the eye lens, each diffraction zone having a principal sub-zone and a phase sub-zone, wherein the diffractive optical structure in the first lens region is designed such that at a design wavelength there is a significant diffraction efficiency for an optical path length difference between the first principal sub-zones of more than one wavelength and averaged over all diffraction zones the principal sub-zones make up a proportion of the diffraction zones of at least 94%, and wherein the diffractive optical structure is designed in such a way that in the first lens region that at the design wavelength there is no significant diffraction efficiency in orders of diffraction less than or equal to zero.

2. The diffractive eye lens as claimed in claim 1, wherein averaged over all diffraction zones the principal sub-zones make up a proportion of the diffraction zones of at least 95% for the first lens region.

3. The diffractive eye lens as claimed in claim 1, wherein the diffractive optical structure further comprises at least one second lens region including a second ring-shaped diffraction zone circumferential about the principal optical axis of the eye lens, the second diffraction zone having a further principal sub-zone and a further phase sub-zone, wherein averaged over all second diffraction zones the further principal sub-zones make up a proportion of the second diffraction zones of at least 94% for the second lens region and the first lens region and the second lens region differ from one another in at least one of the following optical parameters: an optical path length difference, a zone size.

4. The diffractive eye lens as claimed in claim 3, wherein the at least one second diffraction zone of the second lens region is arranged between two first diffraction zones of the first lens region when viewed in the radial direction around the principal optical axis, the first diffraction zones and the at least one second diffraction zones.

5. The diffractive eye lens as claimed in claim 3, wherein the first diffraction zones and the at least one second diffraction zones are arranged in an alternating sequence when viewed in the radial direction.

6. The diffractive eye lens as claimed in claim 3, wherein the diffractive optical structure is designed in such a way that in the first lens region, in the at least one second lens region or both that at the design wavelength there is no significant diffraction efficiency in negative orders of diffraction, or no significant diffraction efficiency in orders of diffraction less than or equal to zero.

7. The diffractive eye lens as claimed claim 3, wherein all first diffraction zones of the first lens region, all second diffraction zones of the second lens region or both each have the same zone size, each have the same optical path length difference or both.

8. The diffractive eye lens as claimed in claim 1, wherein the respective principal sub-zone makes up the proportion of the respective diffraction zone of at least 94% for all of the first diffraction zones, for all of the at least one second diffraction zones or both.

9. The diffractive eye lens as claimed in claim 1, wherein at the design wavelength there is a significant diffraction efficiencyfor at least two orders of diffractionor at least three orders of diffraction.

10. The diffractive eye lens as claimed in claim 1, wherein a maximum diffraction efficiency is less than 0.3%, in a defocus range, with the defocus range ranging at least from −45 dpt to −15 dpt in relation to a refractive power of the distance focus.

11. The diffractive eye lens as claimed in claim 1, wherein a maximum diffraction efficiency is less than 0.15%, in a defocus range, with the defocus range ranging at least from −60 dpt to −10 dpt in relation to a refractive power of the distance focus or at least from.

12. The diffractive eye lens as claimed in claim 1, wherein an integrated diffraction efficiency is less than 6%, in a defocus range, with the defocus range ranging at least from −45 dpt to −15 dpt in relation to a refractive power of the distance focus.

13. The diffractive eye lens as claimed in claim 1, wherein an integrated diffraction efficiency is less than 2%, in a defocus range, with the defocus range ranging at least from −60 dpt to −10 dpt in relation to a refractive power of the distance focus.

14. The diffractive eye lens as claimed in claim 1, wherein the design wavelength is in a central spectral range of a luminous efficiency function.

15. The diffractive eye lens as claimed in claim 1, wherein the design wavelength is between 530 nm and 570 nm, at 550 nm or at 546 nm.

16. The diffractive eye lens as claimed in claim 15, wherein the design wavelength is at 550 nm or at 546 nm.

17. The diffractive eye lens as claimed in claim 1, wherein the eye lens comprises a biocompatible material and is suitable for implantation in an eye.

18. The diffractive eye lens as claimed in claim 1, wherein the eye lens comprises a contact lens, an intraocular lens or an intracorneal lens.

19. A method for producing a diffractive eye lens as claimed in claim 1, comprising:

providing an eye lens blank, removing material from the eye lens blank to produce a diffraction zone of the diffractive structure using a tool with a radius corresponding to no more than 6%, of the width of the diffraction zone.

20. The method for producing a diffractive eye lens as claimed in claim 19, comprising: removing material from the eye lens blank to produce a diffraction zone of the diffractive structure using a tool with a radius corresponding to no more than 5% of the width of the diffraction zone.

* * * * *